United States Patent [19]

Stern et al.

[11] Patent Number: 5,693,360
[45] Date of Patent: Dec. 2, 1997

[54] TOOTH PICK AND METHOD FOR THE MANUFACTURE THEREOF

[76] Inventors: Leif Einar Stern, Strandvägen 164, S-234 32 Lomma; Sten Gunnar Drennow, Pilegården, S-240 17 Södra Sandby, both of Sweden

[21] Appl. No.: 541,270

[22] Filed: Oct. 12, 1995

[30] Foreign Application Priority Data

Oct. 12, 1994 [SE] Sweden .................. 9403459

[51] Int. Cl.⁶ .......................................... A61C 15/02
[52] U.S. Cl. .................. 427/2.29; 132/321; 427/200; 427/307; 427/462; 427/465
[58] Field of Search ...................... 427/462, 465, 427/2.29, 430.1, 155, 200, 307, 300, 282; 132/321, 329

[56] References Cited

U.S. PATENT DOCUMENTS

| | | | |
|---|---|---|---|
| 2,402,021 | 6/1946 | Compton | 427/430.1 |
| 2,877,740 | 3/1959 | Friderici | 427/462 |
| 4,292,306 | 9/1981 | Faunce | 424/52 |
| 4,307,129 | 12/1981 | Nisigahana et al. | 427/430.1 |
| 4,616,667 | 10/1986 | Tang | 132/89 |
| 4,922,936 | 5/1990 | Buzzi et al. | 132/321 |
| 4,958,402 | 9/1990 | Weihrauch | 15/159 A |
| 5,078,928 | 1/1992 | Balster et al. | 427/348 |
| 5,143,949 | 9/1992 | Grogan et al. | 427/155 |
| 5,144,024 | 9/1992 | Pepper et al. | |

FOREIGN PATENT DOCUMENTS

| | | |
|---|---|---|
| 0198007 | 12/1988 | European Pat. Off. . |
| 0202296 | 1/1989 | European Pat. Off. . |
| 0277156 | 7/1991 | European Pat. Off. . |

Primary Examiner—Diana Dudash
Attorney, Agent, or Firm—Tarolli, Sundheim, Covell, Tummino & Szabo

[57] ABSTRACT

This invention relates to a method for manufacturing a tooth pick (1), whereby the tooth pick (1) has a blade (2) of elastic plastic material, whereby the surface of said blade (2) is provided with bristles (4) which have been brought in contact with the blade (2) through electrostatic attraction, whereby the bristles (4) have been brought to unite with the blade (2) and whereby the blade (2) comprises a brushing portion (5) provided with bristles (4) and furthermore, a cleaning tip (6) without or substantially without bristles. In order to also permit cleaning of very narrow interdental spaces by means of this tooth pick (1) without damaging the gums, the cleaning tip (6) has in its full length or at least substantial parts thereof a rectangular cross section.

19 Claims, 4 Drawing Sheets

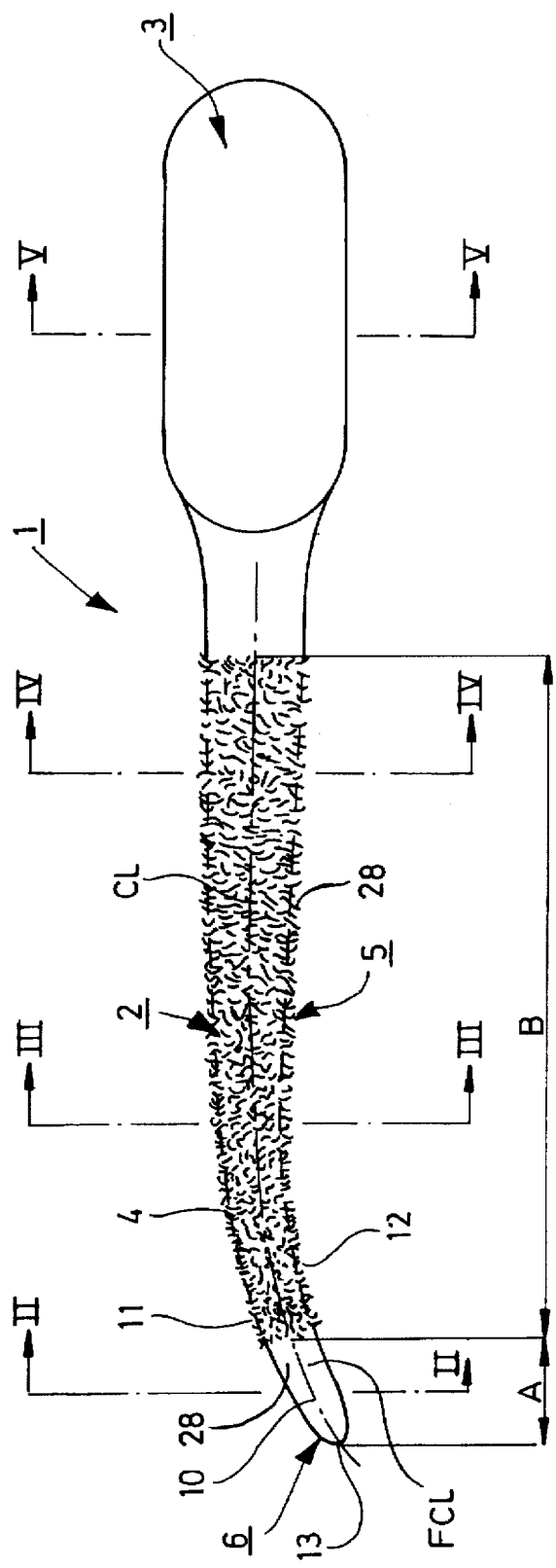
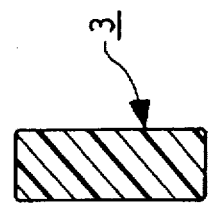
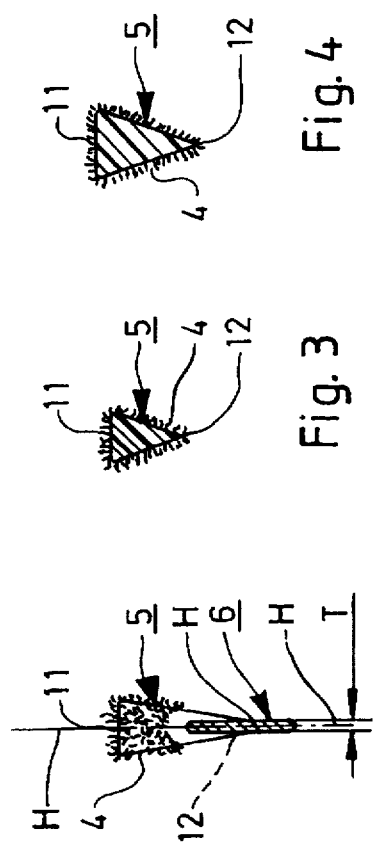

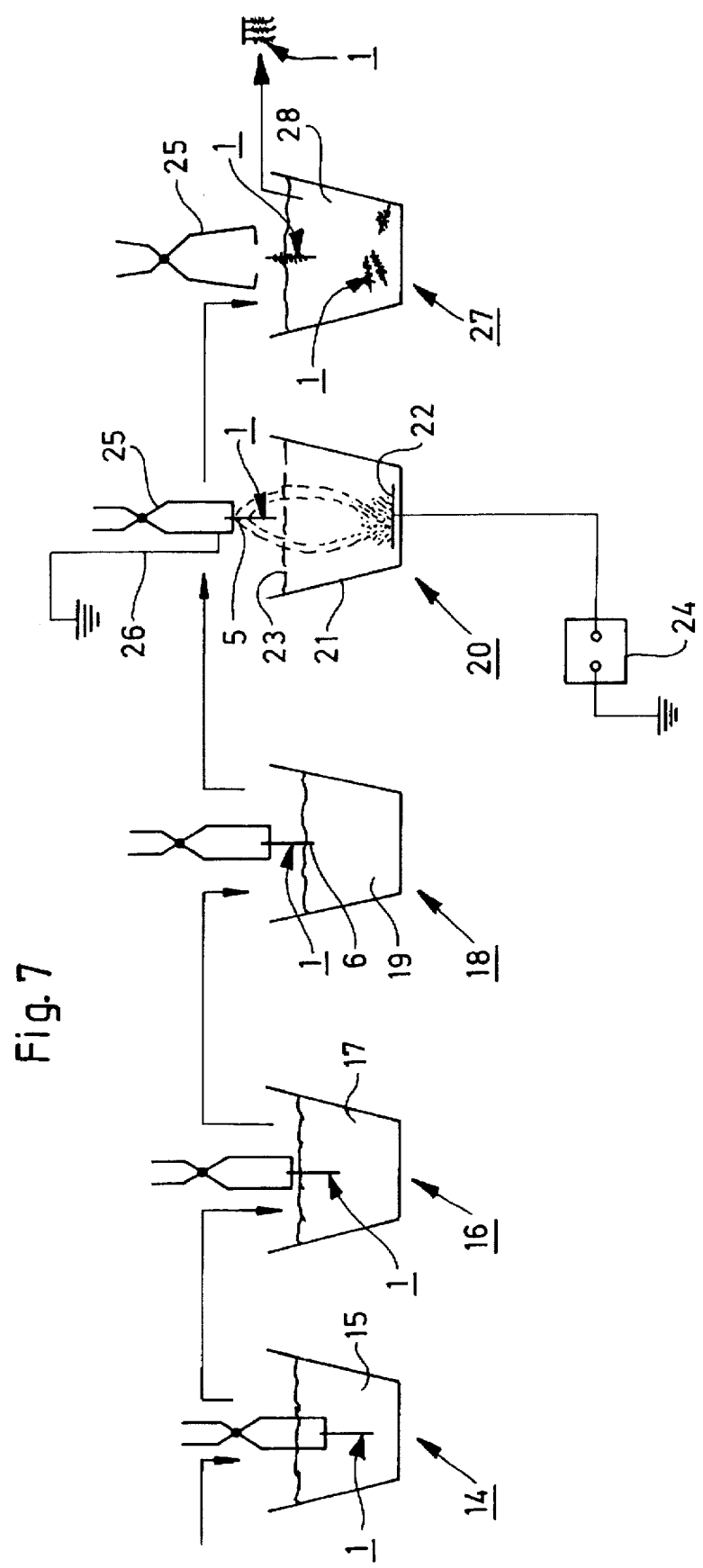

TOOTH PICK AND METHOD FOR THE MANUFACTURE THEREOF

BACKGROUND OF THE INVENTION

1. Field of the Invention

The present invention relates to a tooth pick with a blade of elastic plastic material, whereby the surface of said blade is provided with bristles which preferably have been brought in contact with the blade through electrostatic attraction, whereby the bristles preferably have been brought to unite with the blade, whereby the blade comprises a brushing portion provided with bristles and furthermore, a cleaning tip without or substantially without bristles. The invention also relates to a method for manufacturing this type of tooth pick.

2. Description of the Prior Art

Tooth picks of the abovementioned type and methods for the manufacture thereof are already known from EP-A-0 198 007 and EP-A-0 202 296. These prior art tooth picks function very well in most cases, but it can be difficult to insert them into narrow interdental spaces for efficient cleaning thereof. This is due to the fact that the tooth pick is too thick i.a. because it has bristles all the way to the outermost tip. Except for that these bristles increase the thickness of the front portion of the tooth pick, they also contribute to a large friction between this front portion and the teeth when said front portion is moved into narrow interdental spaces, which further complicates the insertion.

The EP-A-0 277 156 does illustrate tooth picks having a tip without bristles, but this tip is not designed such that it permits efficient cleaning of narrow interdental spaces.

SUMMARY OF THE INVENTION

The object of the present invention has been to eliminate these problems.

The object of the present invention has also been to provide a simple method for quick manufacture of tooth picks.

For a tooth pick according to the invention, it is possible, except for cleaning normal interdental spaces and brushing the tooth portions facing said spaces, to use the tooth pick for cleaning very narrow interdental spaces without damaging the gums.

BRIEF DESCRIPTION OF THE DRAWINGS

The invention will be further described below with reference to the accompanying drawings, wherein FIG. 1 is an enlarged side view of a tooth pick according to the invention;

FIG. 2 is a section along the line II—II through the tooth pick of FIG. 1;

FIG. 3 is a section along the line III—III through the tooth pick of FIG. 1;

FIG. 4 is a section along the line IV—IV through the tooth pick of FIG. 1;

FIG. 5 is a section along the line V—V through the tooth pick of FIG. 1;

FIG. 7 is a schematic view of a device for manufacturing the tooth pick of FIG. 1;

DESCRIPTION OF THE PREFERRED EMBODIMENT

Figure 6:
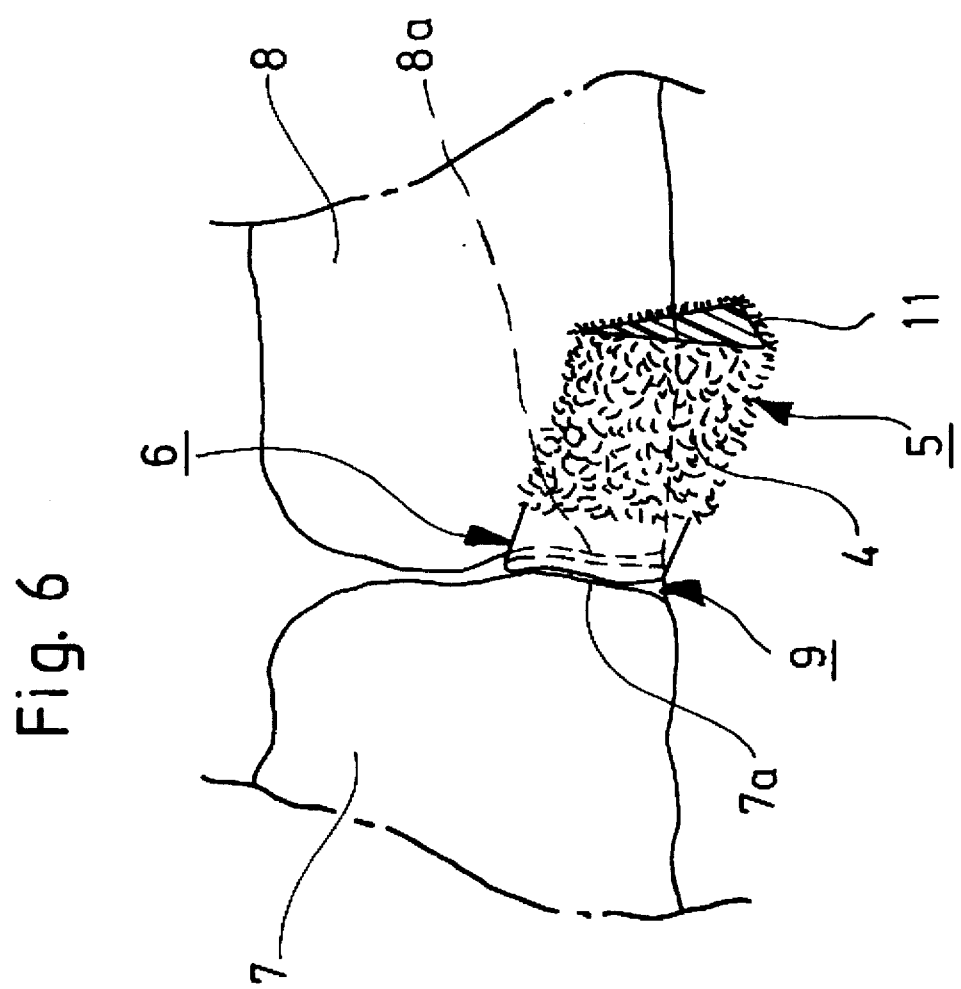
FIG. 6 illustrates a front portion of the tooth pick of FIG. 1 inserted into a narrow interdental space.
Figure 9:
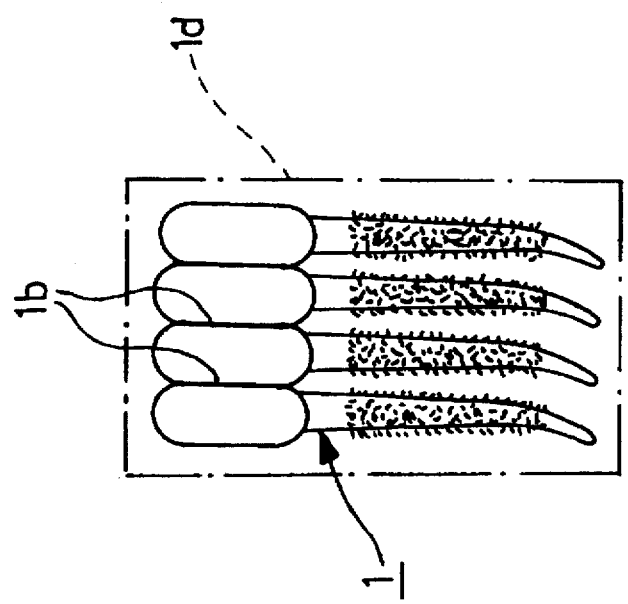
FIG. 9 illustrates a number of tooth picks according to the invention secured to each other and located in a package.
Figure 8:
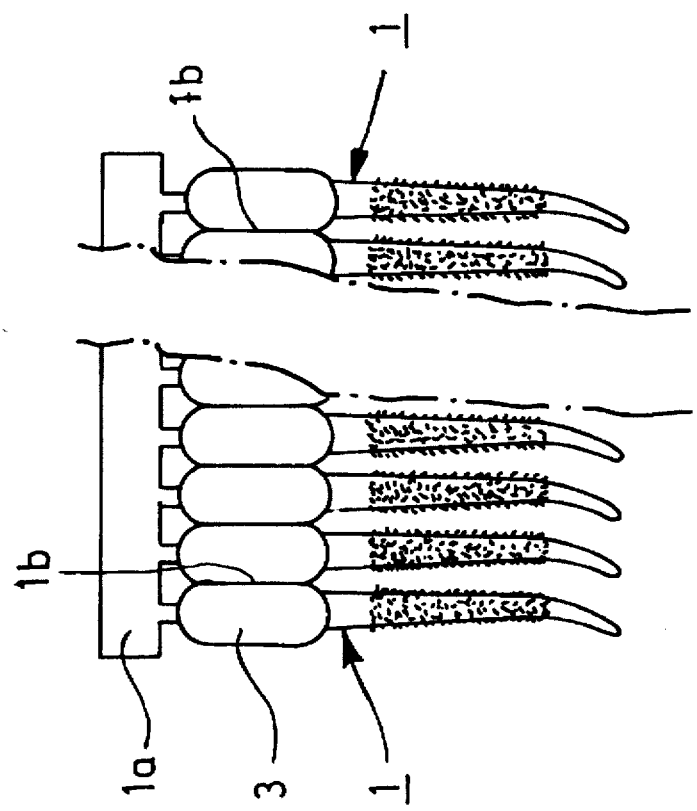
FIG. 8 illustrates a number of tooth picks according to the invention secured to a bracket during a manufacturing method thereof.

In the drawings, a tooth pick 1 having normally a length of 40–60 mm is illustrated in enlargement. The tooth pick 1 may e.g. be about 48 mm long, whereby the blade 2 can be about 32 mm long and the handle member 3 about 16 mm long.

The blade 2 and handle member 3 consist of elastic plastic material, e.g. polyamide/glass-fibre material, and the blade 2 is provided with bristles 4 of plastic material, e.g. of the same or similar plastic material as the blade 2 and handle member 3. The blade 2 is divided into a brushing portion 5 with said bristles 4 and a cleaning tip 6 without or substantially without bristles, said tip being located in front of said brushing portion 5. The brushing portion 5 is i.a. adapted to be inserted into an interdental space 9 between teeth 7, 8 for brushing such parts 7a, 8a of said teeth 7, 8 which face or are directed towards said interdental space 9. The cleaning tip 6 is i.a. adapted to be inserted into the interdental space 9 for cleaning thereof, i.e. for removing e.g. remains of food caught therein, e.g. before brushing of the tooth parts 7a, 8a with the brushing portion 5. In its full length or at least substantial parts thereof, the cleaning tip 6 is rectangular in cross section. Hereby, the cleaning tip 6 can be inserted into those interdental spaces which are too narrow for insertion of the brushing portion 5.

Preferably, the entire or at least substantial parts of the cleaning tip 6 extends/extend arcuately along a fore arcuate centre line FCL. This line proceeds from a centre line CL along the brushing portion 5 and extends therefrom in forward direction and to one side. Longitudinal edges of the cleaning tip 6 are softly rounded and the cleaning tip or at least substantial parts thereof tapers/taper successively in forward direction towards a softly rounded outer end portion 13.

Preferably, the entire or at least substantial parts of the brushing portion 5 extends/extend in a straight forward direction along a straight centre line CL, whereby the brushing portion 5 or at least substantial parts thereof preferably tapers/taper successively in a forward direction towards the cleaning tip 6.

The cleaning tip 6 preferably has a smoother surface 10 than the brushing portion 5, i.a. because it has no bristles 4, in order to ensure that the friction between the cleaning tip 6 and the tooth parts 7a, 8a is less than the friction between the brushing portion 5 and said tooth parts 7a, 8a when the tooth pick is inserted into the interdental space 9.

The cleaning tip 6 is preferably completely or at least partially more flexible than the brushing portion 5 or than substantial parts of the brushing portion 5, so that the cleaning tip 6, by bending, can adapt or adjust to narrow and/or bent interdental spaces 9. The brushing portion 5 has such rigidity that it permits insertion of the cleaning tip 6 in said interdental spaces 9 without bending.

The cleaning tip 6 is preferably substantially shorter than the brushing portion 5. Thus, the cleaning tip 6 can be at least 1 mm long and preferably 2–8 mm (the length of the cleaning tip 6 is designated A in FIG. 1), while the brushing portion 5 can be at least 18 mm long (the length of the brushing portion 5 is designated B in FIG. 1).

The brushing portion 5 preferably has a triangular cross section, whereby the base 11 of the triangle defines a blade side or blade surface while the apex of the triangle defines an opposite blade side or surface. The size of the base 11 of the triangle decreases preferably successively in direction towards the cleaning tip and is least at the blade 2 closest thereto. The base 11 of the triangle is, at the parts of the blade 2 located closest to the handle member 3, substantially larger than the thickness of the cleaning tip 6.

The cleaning tip 6 or at least parts thereof extends/extend, seen in a plan view from the front, along a vertical line H from the base 11 of the triangle to the apex 12 thereof and/or along an extension of said vertical line H beyond the apex 12 of the triangle.

The cleaning tip 6 is preferably of uniform thickness and has preferably a thickness T falling below 20% of the thickest parts of the blade 2. The thickness T is preferably within the range of 0.2–0.4 mm.

The handle member 3 is preferably at least as thick or substantially at least as thick as the part or portion of the blade 2 connected therewith, and the handle member 3 is preferably of uniform thickness or substantially of uniform thickness along its full length. Furthermore, the handle member 3 preferably has a thickness of 1.5–2.5 mm and it is preferably wider than the part of the blade 2 connected therewith. The handle member 3 is suitably at least 14 mm long, preferably 16–24 mm long.

The blade 2 is widest at the handle member 3 and its width decreases successively in the direction towards the outer end portion 13.

The bristles 4 on such a part of the brushing portion 5 which is situated closest to the cleaning tip 6, may be more sparsely located than on other parts of the brushing member 5, whereby the bristles 4 on said part may be increasingly more sparsely located in the direction towards the cleaning tip 6.

During treatment of the tooth pick 1, a plurality of tooth picks can be provided on a bracket 1a and/or can the handle members 3 thereof be attached to each other along break portions 1b.

Tooth picks 1 are suitably placed in packages 1d attached to each other along said break portions 1b or in any other suitable way so that the bristles 4 do not come in contact with each other and so that said tooth picks are easily separated from each other.

Bristles 4 are brought to adhere to the surface of the blade 2 by being attracted thereto by means of electrostatic attraction, i.e. so called flocking, after the surface has been dissolved by such an agent 17 which permits that contact portions of the bristles 4, brought in contact with the dissolved surface, are also dissolved so that the surface and bristles 4 take shape with each other when the dissolved material regains or returns to its original consistency or about its original consistency. This method can be defined as a confounding or fusion between the surface material of the blade and the contact portions of the bristles 4. Hereby, the surface 10 of the cleaning tip 6 is not or not to the same degree dissolved as the surface of the brushing portion 5, in order to, during bristle application, prevent or at least obstruct bristles 4 from adhering to the cleaning tip 6 or at least prevent the bristle coating from becoming as close on said cleaning tip 6 as on the brushing portion 5.

A device for carrying through the bristle application is schematically illustrated in FIG. 7. At this device, each tooth pick 1, which preferably is provided on the bracket 1a along with other tooth picks, is dipped in water 15 in a station 14 for soaking it and thus, allow for making the surface thereof conductive. Thereafter, the tooth picks 1 are moved to station 16 and here dipped in a suitable agent 17, e.g. an organic acid such as formic acid. In this station 16, the blade 2 is dipped in the acid 17, but not the handle member 3. In station 16, the acid 17 brings the surface of the tooth pick 1 to "dissolve", whereby the dissolution of the surface of the brushing portion 5 is utilized for subsequent bristle application, while the dissolution of the surface 10 of the cleaning tip 6 is utilized for cleaning thereof and/or for dissolving eventual projections, burrs or other irregularities therefrom and/or level out or smoothen porosities therein so that the surface 10 becomes smooth and free from sharp edges or similar irregularities.

In a subsequent station 18 the cleaning tip 6 of the tooth picks 1 but not their brushing portion 5 is thereafter dipped in a rinsing agent 19, e.g. water, for washing off the agent 17 from the cleaning tip 6 so that said tip gets such a consistency that the bristles 4 can not "fuse" therewith.

In the following station 20, the bristles 4 are attracted to the tooth pick 1 by means of electrostatic attraction. This is achieved e.g. by holding the tooth pick 1 with the surface of the brushing portion 5 in "dissolved" condition above a container 21 with an electrode 22 at the bottom. In the container 21 there is a large number of bristles 4 and at the top it has a grate or net 23 with such a mesh size that said bristles 4 can pass therethrough. The bristles 4 consist of preferably the same or similar plastic material as the tooth pick 1 and they lie completely loose in the container 1.

The electrode 22 is connected to a source of current 24 and the tooth pick 1 is located above the container 21 at a suitable distance from the electrode 22. When the tooth picks reach this position, their conducting surface is earthed through a bracket 25 which holds the tooth picks 1 in position, and a ground wire 26 extending from said bracket. When current flows to the electrode 22 from the source of current 24, an electric field is generated between the electrode 22 and the conducting surface of the tooth picks 1, whereby bristles 4 are attracted to the tooth picks 1 while said bristles at the same time repel each other and thereby preferably are uniformly distributed over the surface of the brushing portion and preferably directed straight outwards from the tooth picks 1.

With the bristles 4 brought in contact with the dissolved surface of the brushing portion 5, the bristles 4 "fuse" together with said surface when the dissolved material regains or returns to its original consistency or substantially original consistency. Through this so called flocking method, the bristles 4 will be integrated with the surface of the brushing portion 5, so that they can not loosen therefrom.

Finally, the tooth picks 1 provided with bristles 4 can be brought to station 27 for treatment of the tooth picks 1 with an agent 28 containing xylitol and a water soluble fluorine compound. The treatment is suitably carried through by dipping the tooth picks 1 in the agent 28. Hereby, xylitol will effectively bond the fluorine compound at least to particularly the bristles 4, but also to other parts of the tooth pick 1 so that a long-term release of fluorine is obtained during use of the tooth pick 1.

Since xylitol bonds the fluorine compound to the surfaces of the tooth pick 1 and particularly to the bristles 4 with good bonding strength, the tooth pick 1 becomes a tooth cleaning tool as well as a tool for supplying fluorine compound to the teeth when said teeth are cleaned.

There may be a further station (not shown) for washing the tooth picks 1 with a suitable liquid. In the station, such bristles 4 which have adhered to the cleaning tip 6 without being supposed to do so, can be removed by being flushed away.

Instead of exposing the brushing portion 5 as well as the cleaning tip 6 of the tooth pick 1 to said agent 17, the cleaning tip 6 can be provided with a protective agent, e.g. glycerine and/or a petroleum jelly such as vaseline, which prevents the agent 17 from coming in contact with the cleaning tip 6 or at least substantial parts thereof when said agent 17 is applied to the tooth pick 1. The protective agent can be applied to the cleaning tip 6 by dipping said tip in said protective agent, and when the bristle application on to the brushing portion 5 is finished, said agent can be removed from the cleaning tip 6 in a suitable manner, e.g. by dipping said tip in a removing agent.

The invention is not limited to the embodiment of the tooth pick described above and illustrated in the drawings, but said tooth pick may vary within the scope of the following claims, and this is true also for the method for manufacturing the tooth pick 1. As alternatives it should be mentioned that the tooth pick 1 may have other shapes and dimensions than the described and the blade 2 and handle member 3 thereof are preferably manufactured as a unit of the same plastic material, e.g. polyamide material, but also of another plastic material. The bristles 4 may be of the same or similar plastic material as the blade 2, e.g. polyamide material, but they can also consist of another plastic material. Other agents than organic acids can be used as agent 17 for "dissolving" the surface of the blade 2, and this agent can be sprayed on to the tooth picks 1 instead of dipping said tooth picks therein.

We claim:

1. Method for manufacturing tooth picks of plastic material, the tooth picks comprising a brushing portion and a cleaning tip, the brushing portion comprising a brushing portion surface and the cleaning tip comprising a cleaning tip surface, the method comprising:

subjecting the brushing portion surface and the cleaning tip surface of the tooth pick to acid such that a quantity of said acid adheres to and dissolves the brushing portion surface and the cleaning tip surface;

subjecting the cleaning tip surface to a rinsing agent comprising water to flush away said acid from the cleaning tip surface of the tooth pick before adhering the bristles to the tooth pick;

bringing said bristles in contact with the dissolved brushing portion surface and said acid on the dissolved brushing portion surface by electrostatic attraction to adhere said bristles to the brushing portion surface.

2. Method for manufacturing tooth picks, characterized in:

that the tooth pick is made of a plastic material and is brought to comprise a brushing portion and a cleaning tip in front of the brushing portion, whereby the brushing portion is given a triangular cross section and said cleaning tip a flat and substantially thinner cross section than said brushing portion;

that the brushing portion is subjected to an agent which dissolves the surface of the plastic material of said brushing portion;

that the surface of the plastic material of the cleaning tip is not dissolved;

that bristles of the same or a different plastic material are adhered to the dissolved surface of the plastic material of the brushing portion by means of electrostatic attraction but are prevented from adhering to the surface of the cleaning tip since this surface is not dissolved; and that the brushing portion of the tooth pick and the bristles adhering thereto are provided with an agent containing xylitol and a fluorine compound, whereby the xylitol is used as a bactericide as well as an agent for bonding the fluorine compound to the brushing portion and to the bristles adhering to said brushing portion.

3. Method according to claim 2, characterized in that the tooth pick and said bristles are made of a polyamide material.

4. Method according to claim 2, characterized in that the tooth pick is made of a composite of a polyamide material and a glass fiber material.

5. Method according to claim 2, characterized in that an organic acid is used as said first agent for dissolving the first surface of the plastic material of the brushing portion.

6. Method according to claim 5, characterized in that the organic acid is formic acid.

7. Method according to claim 2, characterized in that the brushing portion and the cleaning tip are formed as an arcuate blade which tapers in the forward direction.

8. Method for manufacturing tooth picks, characterized in that the tooth pick is made of a plastic material and comprises a brushing portion and a cleaning tip extending axially from the brushing portion, whereby the brushing portion includes a first surface having a triangular cross section and the cleaning tip includes a second surface having a flat cross section which is substantially thinner than the brushing portion, the method comprising;

subjecting the brushing portion to a first agent to dissolve the first surface of the brushing portion while preventing the second surface of the cleaning tip from being subjected to said first agent thereby preventing the second surface from being dissolved;

adhering bristles of the same or of a different plastic material by electrostatic attraction to the dissolved first surface of the brushing portion, said bristles being prevented from adhering to the second surface of the cleaning tip since the second surface is not dissolved by said first agent; and subjecting the brushing portion of the tooth pick and said bristles adhering thereto to a second agent containing xylitol and a fluorine compound, xylitol acting as a bactericide as well as a means for bonding the fluorine compound to the brushing portion and to said bristles adhering to the brushing portion.

9. Method according to claim 8, characterized in that the tooth pick and said bristles are made of a polyamide material.

10. Method according to claim 8 characterized in that the tooth pick is made of a composite of a polyamide material and a glass fiber material.

11. Method according to claim 8, characterized in that said first agent for dissolving the surface of the plastic material of the brushing portion is an organic acid.

12. Method according to claim 11, characterized in that the organic acid is formic acid.

13. Method according to claim 8, characterized in that the brushing portion and the cleaning tip are formed as an arcuate blade which tapers in the forward direction.

14. Method according to claim 8 wherein said step of subjecting the brushing portion to said first agent to dissolve the first surface of the brushing portion while preventing the second surface of the cleaning tip from being subjected to said first agent thereby preventing the second surface from being dissolved comprises submerging both the brushing portion and the cleaning tip in said first agent, the cleaning tip being covered by a protective agent to prevent said first agent from coming in contact with and adhering to the cleaning tip surface.

15. Method according to claim 14 wherein said protective agent is selected from the group consisting of glycerins or petroleum jelly.

16. Method according to claim 14 wherein the tooth pick further comprises a base portion, the brushing portion being disposed axially between the base and the cleaning tip.

17. Method for manufacturing a tooth pick made of a plastic material and comprising a brushing portion and a cleaning tip extending axially from the brushing portion comprising the steps of providing an elongate plastic member having a first surface having a triangular cross section defining the brushing portion and a second surface having a flat cross section, substantially thinner than the triangular cross section of the brushing portion and defining the cleaning tip;

subjecting the brushing portion to a first agent which dissolves the first surface of the plastic material of the brushing portion;

preventing the second surface of plastic material of the cleaning tip from dissolving;

adhering bristles of the same or a different plastic material by electrostatic attraction to the dissolved first surface of the plastic material of the brushing portion while preventing the bristles from adhering to the second surface of the cleaning tip since the second surface of the cleaning tip is not dissolved by the first agent; and providing the brushing portion of the tooth pick and the bristles adhering thereto with a second agent containing xylitol, a bactericide, and a fluorine compound, and bonding the fluorine compound to the brushing portion and to the bristles adhering to the brushing portion by the xylitol.

18. Method according to claim 17 wherein the tooth pick further comprises a base portion, the brushing portion being disposed axially between the base and the cleaning tip.

19. Method according to claim 18, characterized in that the brushing portion and the cleaning tip are formed as an arcuate blade which tapers in the forward direction.

* * * * *